United States Patent
Rochette et al.

(10) Patent No.: US 10,724,954 B2
(45) Date of Patent: Jul. 28, 2020

(54) APPARATUS FOR OPTICAL DETECTION OF BIO-CONTAMINANTS BASED UPON MEASUREMENT OF SATURATION OF LIGHT INTENSITIES AT FLUORESCENCE WAVELENGTH RELATIVE TO LIGHT INTENSITIES AT A PREDETERMINED WAVELENGTH

(71) Applicants: STERIS Inc., Temecula, CA (US); NATIONAL OPTICS INSTITUTE, Quebec (CA)

(72) Inventors: Daniel Rochette, Painesville, OH (US); Pascal Gallant, Quebec (CA); Ozge Mermut, Quebec (CA); Francois Baribeau, Quebec (CA); Isabelle Noiseux, Saint-Augustin-de-Desmaures (CA); Isabelle Gosselin, Ste-Brigitte-de-Laval (CA)

(73) Assignees: STERIS Inc., Temecula, CA (US); INSTITUT NATIONAL D'OPTIQUE/NATIONAL OPTICS INSTITUTE, Quebec (CA)

(*) Notice: Subject to any disclaimer, the term of this patent is extended or adjusted under 35 U.S.C. 154(b) by 282 days.

(21) Appl. No.: 15/678,254

(22) Filed: Aug. 16, 2017

(65) Prior Publication Data
US 2018/0011023 A1  Jan. 11, 2018

Related U.S. Application Data

(60) Division of application No. 15/232,091, filed on Aug. 9, 2016, which is a division of application No.
(Continued)

(51) Int. Cl.
    G01N 21/64   (2006.01)
    G01N 21/94   (2006.01)
    A61L 2/28    (2006.01)

(52) U.S. Cl.
    CPC ............ *G01N 21/6428* (2013.01); *A61L 2/28* (2013.01); *G01N 21/6486* (2013.01);
    (Continued)

(58) Field of Classification Search
    None
    See application file for complete search history.

(56) References Cited

U.S. PATENT DOCUMENTS

| 2,600,221 A | 6/1952 | Domingo ..................... 250/71 |
| 4,932,227 A | 6/1990 | Hogrefe ..................... 68/17 R |

(Continued)

FOREIGN PATENT DOCUMENTS

| EP | 0697590 A1 | 2/1996 | |
| WO | WO 2012/022945 | 2/2012 | ............ G01N 33/50 |
| WO | WO 2012/022963 | 2/2012 | ............ G01N 21/64 |

OTHER PUBLICATIONS

PR Newswire, United Business Media, "Block Engineering Announces Collaborative Agreement with Pfizer for Next Generation Cleaning Verification Technology," article obtained from website www.prnewswire.com/news-releases/block-engineering-announces-collaborative-agreement-with-pfizer-for-next-generation-cleaning-verification-teehnology-187438201.html, last accessed Mar. 18, 2013.
(Continued)

*Primary Examiner* — Xiaoyun R Xu
(74) *Attorney, Agent, or Firm* — Kusner & Jaffe

(57) ABSTRACT

A method for optical detection of residual soil on articles (such as medical instruments and equipment), after completion of a washing or a rinsing operation by a washer. A soil detection system provides an indication of soil on the
(Continued)

articles by detecting luminescent radiation emanating from the soil in the presence of ambient light.

13 Claims, 9 Drawing Sheets

Related U.S. Application Data

15/142,309, filed on Apr. 29, 2016, which is a continuation of application No. 13/777,053, filed on Feb. 26, 2013, now Pat. No. 9,354,182.

(52) U.S. Cl.
CPC .......... *G01N 21/94* (2013.01); *A61L 2202/24* (2013.01); *G01N 2021/6417* (2013.01); *G01N 2021/6439* (2013.01); *G01N 2201/068* (2013.01); *G01N 2201/0697* (2013.01); *G01N 2201/06113* (2013.01); *G01N 2201/10* (2013.01); *G01N 2201/105* (2013.01)

(56) References Cited

U.S. PATENT DOCUMENTS

| | | | | |
|---|---|---|---|---|
| 4,938,224 A | 7/1990 | Rysavy | | 128/633 |
| 5,225,675 A | 7/1993 | O'Donnell | | 250/302 |
| 5,396,178 A | 3/1995 | Rybarski | | 324/439 |
| 5,747,794 A | 5/1998 | Malchesky | | 250/227.23 |
| 5,749,385 A | 5/1998 | Rochette et al. | | 134/199 |
| 5,759,289 A | 6/1998 | Caron et al. | | 134/34 |
| 5,863,790 A | 1/1999 | Bolea | | 435/287.4 |
| 5,900,067 A | 5/1999 | Jones | | 134/1 |
| 5,906,802 A | 5/1999 | Langford | | 422/300 |
| 5,923,432 A | 7/1999 | Kral | | 356/432 |
| 5,928,948 A | 7/1999 | Malchesky | | 436/2 |
| 6,021,344 A | 2/2000 | Lui | | 351/159.3 |
| 6,394,111 B1 | 5/2002 | Jacobs et al. | | 134/113 |
| 6,454,874 B1 | 9/2002 | Jacobs et al. | | 134/18 |
| 6,494,964 B1 | 12/2002 | Jacobs et al. | | 134/18 |
| 6,516,817 B2 | 2/2003 | Jacobs et al. | | 134/113 |
| 6,516,818 B2 | 2/2003 | Jacobs et al. | | 134/113 |
| 6,524,390 B1 | 2/2003 | Jones | | 134/1 |
| 6,571,812 B1 | 6/2003 | Lavoie et al. | | 134/191 |
| 6,653,146 B1 | 11/2003 | Ruvinsky et al. | | 436/172 |
| 6,666,218 B2 | 12/2003 | Lavoie et al. | | 134/25.2 |
| 6,683,735 B2 | 1/2004 | Stuckey | | 359/831 |
| 6,737,645 B2 | 5/2004 | Foster et al. | | 250/302 |
| 7,439,217 B2 | 10/2008 | Boutique et al. | | 510/287 |
| 2003/0135092 A1 | 7/2003 | Cline et al. | | 600/160 |
| 2003/0185966 A1 | 10/2003 | Kim et al. | | 427/8 |
| 2003/0205682 A1 | 11/2003 | Kapoor et al. | | 250/458.1 |
| 2004/0010192 A1 | 1/2004 | Benaron | | 600/431 |
| 2006/0153508 A1 | 7/2006 | Bowker et al. | | |
| 2007/0109536 A1 | 5/2007 | Weiss et al. | | 356/318 |
| 2008/0061236 A1 | 3/2008 | Meredith et al. | | 250/338.1 |
| 2009/0109408 A1 | 4/2009 | Hsiung | | 353/84 |
| 2010/0252437 A1 | 10/2010 | Amirkhanian et al. | | |
| 2012/0021406 A1 | 1/2012 | Franciskovich et al. | | 435/5 |
| 2012/0033220 A1 | 2/2012 | Kotidis et al. | | 356/445 |
| 2012/0315627 A1 | 12/2012 | Aojula et al. | | 435/5 |
| 2016/0349179 A1 | 12/2016 | Rochette et al. | | |
| 2018/0067051 A1 | 3/2018 | Baribeau | | |

OTHER PUBLICATIONS

Website print out of "Proreveal Fluorescence Protein Detection Test Overview," www.synopticshealth.com/overview/, print out date Oct. 28, 2013.

Website print out of "Synoptics Health Proreveal Technical FAQs," www.synopticshealth.com/faqs, print out date Oct. 28, 2013.

Website print out of "ProReveal Fluorescence Protein Detection Test Technical Data Sheet," www.synopticshealth.com/assets/doc/Proreveal-tech-sheet-final.pdf, print out date Oct. 28, 2013.

Novak et al., "An integrated fluorescence detection system for lab-on-a-chip applications," 2007, Lab on a Chip, vol. 7, pp. 27-29.

Fujiki et al., Quantification of Green Fluorescent Protein by In Vivo Imaging, PCR, and Flow Cytometry: Comparison of Transgenic Strains and Relevance for Fetal Cell Microchimerism, 2008, Cytometry Par A, vol. 74A, pp. 111-118.

APPARATUS FOR OPTICAL DETECTION OF BIO-CONTAMINANTS BASED UPON MEASUREMENT OF SATURATION OF LIGHT INTENSITIES AT FLUORESCENCE WAVELENGTH RELATIVE TO LIGHT INTENSITIES AT A PREDETERMINED WAVELENGTH

RELATED APPLICATIONS

The present application is a divisional of U.S. application Ser. No. 15/232,091, filed Aug. 9, 2016 (now U.S. Pat. No. 10,048,203, issued Aug. 14, 2018), which is a divisional of U.S. application Ser. No. 15/142,309, filed Apr. 29, 2016 (now U.S. Pat. No. 10,036,705, issued Jul. 31, 2018), which is a continuation of U.S. application Ser. No. 13/777,053, filed Feb. 26, 2013 (now U.S. Pat. No. 9,354,182, issued May 31, 2016), said patent application fully incorporated herein by reference.

FIELD OF THE INVENTION

The present invention relates generally to the cleaning and decontaminating arts, and more particularly to a method and apparatus for optical detection of biological contaminants on articles, such as medical devices, food, agricultural products, forensic equipment and devices, and the like, after undergoing a decontamination process.

BACKGROUND OF THE INVENTION

Medical washers are conventionally known and are used to clean articles (e.g., medical devices, such as medical instruments and equipment) that have been exposed to bio-contaminants. Such washers typically clean the articles to remove bio-contaminants by directing jets or streams of fluid at the articles from spray heads or nozzles located within the washer. A typical cleaning operation may include a preliminary rinse cycle, a pre-wash cycle, a wash cycle, a post-wash rinse cycle, a thermal rinse cycle and a drying cycle. During the rinse and wash cycles the articles are exposed to one or more chemical cleaning and rinsing solutions.

It is not unusual for a cleaning operation to be followed by a visual inspection conducted by a human to insure that there are no residual bio-contaminants (hereinafter referred to as "soil") on the articles. The soil may include organic residues including, but not limited to, blood, fat, mucous, lipids, carbohydrates, bone, hair, protein, and food product. Some articles have unique shapes, corners or crevices that make removal of the bio-contaminants therefrom difficult. Human visual inspection helps ensure that post-wash articles with soil thereon are not allowed to proceed to further processing (e.g., sterilization) without first removing any remaining bio-contaminants.

As will be appreciated, a human visual inspection is both time-consuming and costly. Moreover, it is difficult to detect minute amounts of soil by human visual inspection, and such visual inspection is subject to human error (for example, person-to-person variations and individual biases). Furthermore, it is observed that human visual inspection is a binary qualitative process, not quantitative.

Some prior art methods for optical detection of soil use a fluorescent dye or agent to detect the presence of soil on an article. In such systems, the fluorescent agent is applied to the article, for example, by exposing the article to a solution that includes the fluorescent agent. The fluorescent agent binds to organic residues (e.g., proteins), and thus affixes to the soil to label the bio-contaminant. Where there is no soil on the article, the fluorescent agent does not become affixed thereto, and thus can be washed off. To provide optical detection of the soil according to prior art methods, the article is exposed to "black light" (i.e., electromagnetic radiation in the ultraviolet range having wavelengths around 315-400 nm), which is absorbed by the fluorescent agent. Absorbance of this ultraviolet (UV) light causes the fluorescent agent (e.g., a fluorophore such as fluorescein) to emit visible light (i.e., to be fluorescent), thereby identifying the presence of soil to a human inspector. A typical human eye is responsive to light in the wavelength range of 390-750 nm.

This prior art method does not allow personnel to carry out their task of reprocessing of articles in desirable ambient light conditions, and thus makes it difficult for personnel to disassemble, reassemble, and inspect articles for cleanliness. Recommended illuminance levels for such work environments can range from 200 lux to 2000 lux, and more typically range from 1400 lux to 2000 lux.

The present invention provides a method and apparatus for optical detection of soil that operates in preferred ambient lighting conditions.

SUMMARY OF THE INVENTION

According to a first aspect of the present invention, there is provided a soil detection system for detecting presence of soil on an article, the soil detection system comprising: (a) a scanning unit including: a light source for producing light to be incident on the article; a detector for detecting electromagnetic radiation emanating from said article and generating light data corresponding thereto, said electromagnetic radiation including ambient light reflected by the article and light emitted by an excited luminescent agent that is bound to the soil, and a light filter for filtering light of predetermined frequencies; and (b) a control unit for receiving the light data generated by the detector to determine the presence of soil on the article.

According to another aspect of the present invention, there is provided a method for detecting presence of soil on an article, said method comprising: introducing a luminescent agent to a detergent during a wash cycle of a washing apparatus, wherein the luminescent agent is bound to soil present on the article; rinsing the article to remove unbound luminescent agent; exposing the article to laser light; detecting light emanating from said article and generating light data corresponding thereto, said light emanating from said article including ambient light reflected by the article and light emitted by exciting the luminescent agent bound to the soil; filtering the light emanating from said article at predetermined frequencies; and determining the presence of soil on the article based upon the filtered light received by a light detector.

An advantage of the present invention is the provision of a method and apparatus that uses optical excitation and luminescence (such as fluorescence) to detect the presence of soil on articles that have undergone a washing or rinsing process.

Still another advantage of the present invention is the provision of a method and apparatus that allows optical detection of soil on articles in the presence of ambient light.

These and other advantages will become apparent from the following description of the present invention, taken together with the accompanying drawings and the appended claims.

BRIEF DESCRIPTION OF THE DRAWINGS

The present invention may take physical form in certain parts and arrangement of parts, preferred embodiments of which will be described in detail in the specification and illustrated in the accompanying drawings which form a part hereof, and wherein.

DETAILED DESCRIPTION OF THE INVENTION

It should be appreciated that the term "medical devices" as used herein, includes, but is not limited to, such articles as surgical, dental, veterinary and mortuary instruments and equipment. The articles may be made of various materials, including, but not limited to, stainless steel.

Figure 1:
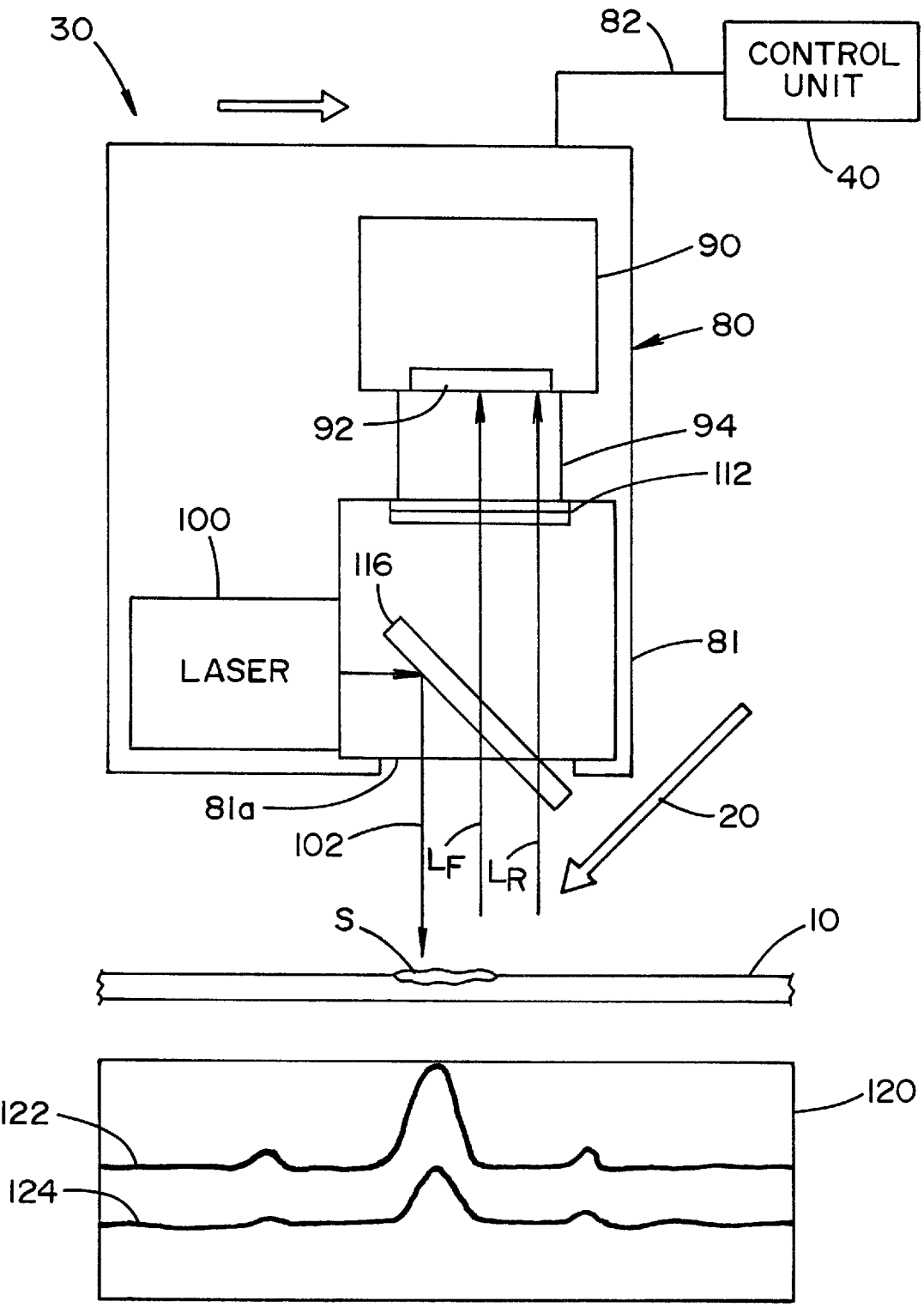
FIG. 1 is a schematic view of a soil detection system according to a first embodiment of the present invention.
Figure 3:
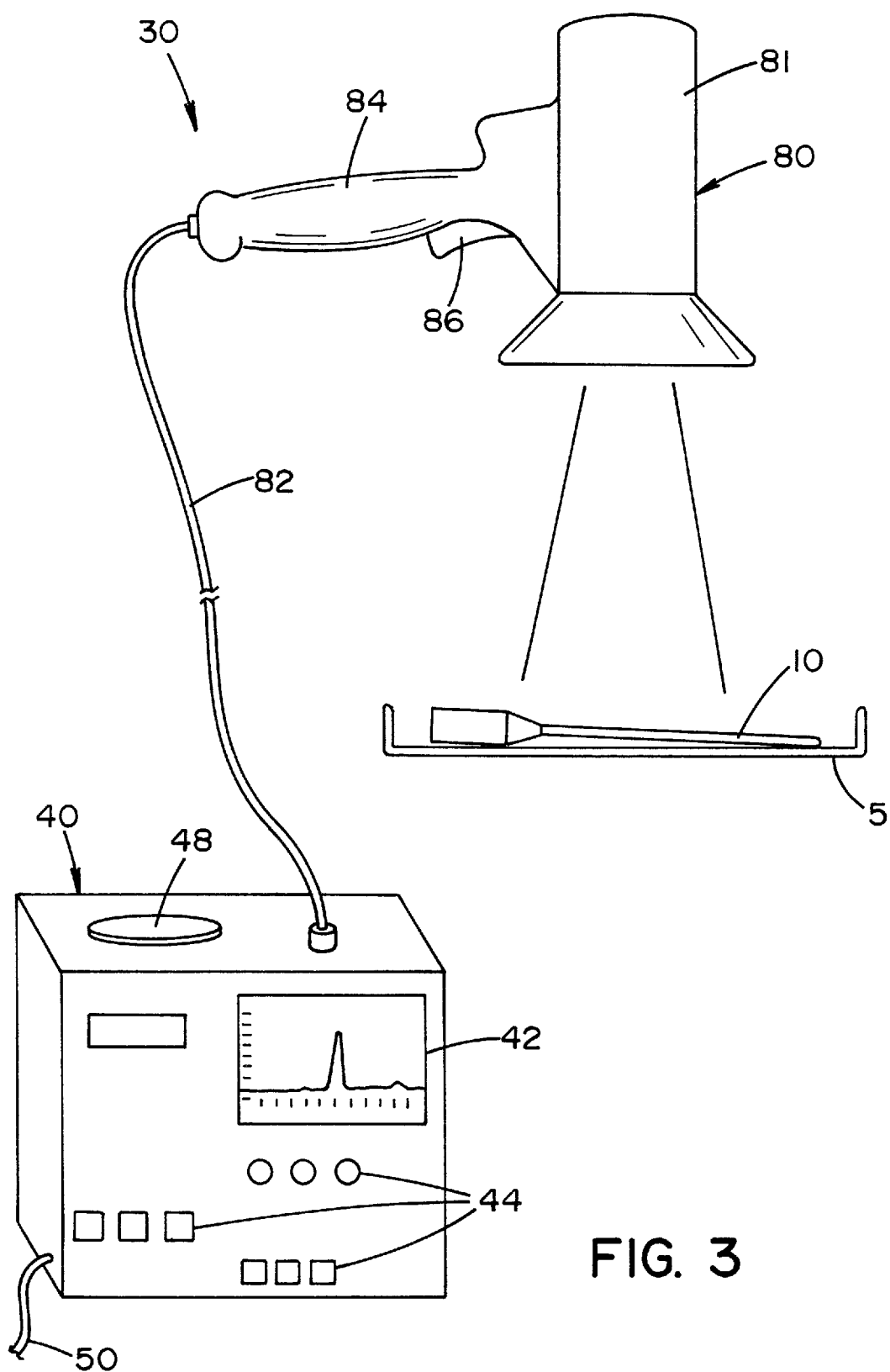
FIG. 3 is a detailed illustration of a soil detection system according to the first embodiment of the present invention.
Figure 4A:
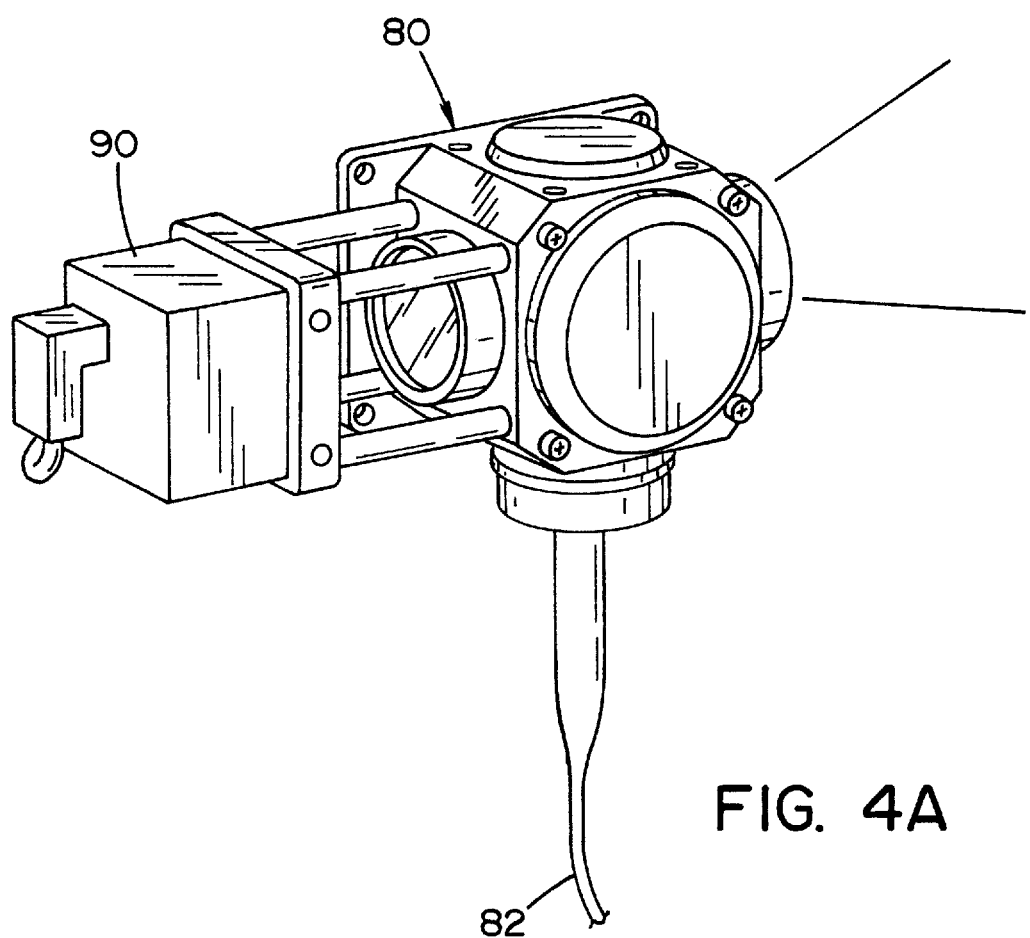
FIGS. 4A and 4B illustrate internal components of a scanning unit for the soil detection system.
Figure 4B:
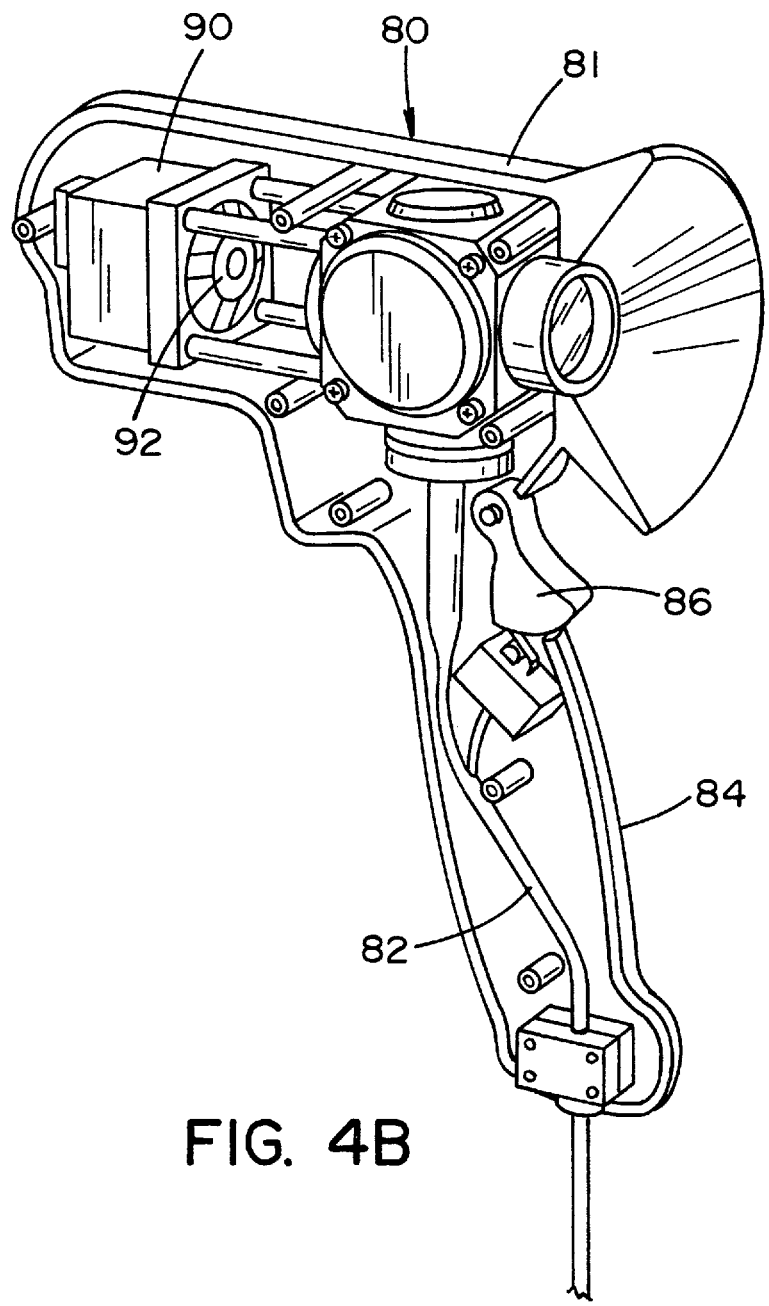

Referring now to FIGS. 1 and 3, there is shown a soil detection system 30 according to an embodiment of the present invention, generally comprised of a scanning unit 80 and a control unit 40. Scanning unit 80 includes a detector 90, a light source in the form of a laser 100 that produces a laser light 102, a light filter 112, and a dichroic beamsplitter 116 that are located within a housing 81. In the illustrated embodiment, scanning unit 80 is handheld by the user. It should be understood that the light source can alternatively be located external to scanning unit 80 and an optical fiber used to transmit light from the external light source to scanning unit 80.

In the illustrated embodiment, detector 90 takes the form of a conventional digital video/still camera that includes a CMOS (complementary metal-oxide semiconductor) or CCD (charge-coupled device) image sensor 92 and a lens 94. A CCD image sensor 92 represents pixels by p-doped MOSFET capacitors. These capacitors are biased above the threshold for inversion when image acquisition begins, allowing the conversion of incoming photons into electron charges at the semiconductor-oxide interface. Image sensor 92 is then used to read out these charges. Detector 90 is adapted to detect electromagnetic radiation emanating from said articles and generate corresponding information (i.e., light data) that is delivered to control unit 40. It should be understood that detector 90 may take the form of any suitable device able to detect electromagnetic radiation and produce an image, including, but not limited to, a CMOS sensor, a CCD, a photodiode, and a photodiode array. In the illustrated embodiment, image sensor 92 takes the form of a color image sensor, such as CCD or CMOS with RGB (Red-Green-Blue) pixel matrix, or a three-dimensional image sensor where color RGB planes are stacked on the same chip, such as 3-CCD or 3-CMOS. These image sensors provide access to each color channel individually for image processing.

In the illustrated embodiment, laser 100 is preferably a laser diode that predominantly emits light ("laser light") at a wavelength of 488 nm (blue). As will be explained in further detail below, the laser light excites a fluorescent agent (e.g., a fluorophore such as fluorescein). Two- and three-dimensional images may be obtained since fluorescence takes place in all directions (i.e., the fluorescence signal is usually isotropic). Furthermore, the signal-to-noise ratio of the fluorescence signal is very high, providing a good sensitivity. In the illustrated embodiment, the fluorescent agent is fluorescein, which has a maximum excitation at light having a wavelength of about 490 nm. Once excited, the fluorescein emits light at a wavelength of about 513 nm. Since the emitted, fluorescent light is of a different frequency than the excitation light, the excitation light can be filtered out. The intensity of light emitted from a region having the fluorescent agent is correlated to the intensity of excitation energy and to the concentration of the fluorescent agent.

It should be understood that the light source of the present invention for producing light emitted by scanning unit 80 may take a number of different forms, including, but not limited to, any kind of device being able to emit a monochromatic or broadband electromagnetic field. Examples of such devices include lasers, solid-state lasers, laser diodes, argon ion lasers, micro wire lasers, diode solid-state lasers, vertical cavity surface emitting lasers, light emitting diodes (LED), organic light emitting diode (OLED), polymer light emitting diode (PLED), quantum dot based light sources, white light sources, halogen lamps, phosphor-coated LEDs, thin-film electroluminescent devices, phosphorescence OLEDs, inorganic/organic LEDs, LEDs using quantum dot technologies, LED arrays, flood light systems using LEDs, white LEDs, filament lamps, arc lamps, gas lamps and fluorescent tubes.

Dichroic beamsplitter 116 is used to both reflect and filter light, depending upon the direction the light is traveling toward dichroic beamsplitter 116. In one direction, dichroic beamsplitter 116 reflects blue light emitted by laser 100 to direct laser light 102 through an opening 81a in housing 81. In a second direction, dichroic beamsplitter 116 cuts blue light and allows green and red light to pass therethrough for reception by detector 90. Accordingly, dichroic beamsplitter 116 prevents any excitation light (in this case, blue light emitted by laser 100) from being received by detector 90. It should be appreciated that a combination of a reflective member (e.g., a dichroic mirror) and one or more light filters may be substituted for dichroic beamsplitter 116. In the embodiment illustrated in FIG. 1, filter 112 is preferably a dual band filter that permits only red and green light to pass therethrough and be received by detector 90.

As shown in FIG. 3, housing 81 includes a handle grip 84. A trigger 86 is provided to activate scanning unit 80, as will be explained below. A cable 82 electrically connects scanning unit 80 with control unit 40.

In the illustrated embodiment of the present invention, control unit 40 includes a display unit 42 (e.g., an LCD or LED display unit), a user input interface 44 (e.g., buttons, knobs, keypad, and the like) for control and programming of control unit 40, and an audio output 48 (e.g., a speaker) for emitting audible sounds. A power cord 50 connects control unit 40 to a power source (e.g., a conventional AC electrical outlet). The power source may also supply power to scanning unit 80 through control unit 40. Control unit 40 includes a processing unit and data storage to perform image processing on the light data collected by detector 90 and provides an audible and/or visual soil detection feedback using audio output 48 and display unit 42. A detailed description of the operation of control unit 40 and scanning unit 80 is provided below.

The present invention will now be further described with reference to detection of soil on articles that have been exposed to a solution containing a fluorescent agent (e.g., fluorescein, which is biocompatible). For example, a medical washer (washing apparatus) may be provided to remove bio-contaminants from articles placed in a washing chamber by directing jets or streams of fluid at the articles from spray heads or nozzles located within the washer chamber. The washer may be configured to expose the articles to a solution containing the fluorescent agent during the washer's standard wash cycle and/or rinse cycle. The fluorescent agent (non-specifically) binds to organic residues (e.g., proteins), and thus affixes to soil on the articles to label the bio-contaminant. Where there is no soil on the article, the fluorescent agent does not become affixed thereto (i.e., is unbound), and therefore can be easily rinsed off of the article. In a preferred embodiment, no extra wash time is required for labeling the bio-contaminant and no extra rinse time is required to remove all of the unbound fluorescent agent. Accordingly, no changes are required of existing medical washers with respect to standard wash and rinse cycles (i.e., no additional "marking" cycle, or pre-wash cycle, etc. is required). In one embodiment of the present invention, fluorescein is used as the fluorescent agent at a concentration in the range of about 0.001 mM to 90 mM (for example, around 0.3 mM) with an exposure time in the range of 30 seconds to 5 minutes to label the bio-contaminant.

It is contemplated that the washer may include a source of a fluorescent agent that is introduced into a water inlet line to the washing chamber during a desired stage of the washing and/or rinsing cycles. A valve controls the flow of the fluorescent agent into the water inlet line. Preferably, the solution containing the fluorescent agent is introduced into the washing chamber during a later stage of the washing cycle. Therefore, during a subsequent rinsing cycle, the fluorescent agent can be removed from unsoiled portions of the articles. The solution containing the fluorescent agent may be combined with a washing solution that includes a decontaminating agent or cleaning detergent. The decontaminating agent or cleaning detergent may initially be in a liquid or dry powder form. The fluorescent agent may be directly added to the decontamination or cleaning detergent before the detergent is added to the washing chamber.

It should be appreciated that while an illustrated embodiment of the present invention is described herein with reference to "fluorescein" as the fluorescent agent, it is contemplated that alternative fluorescent agents may be substituted for fluorescein. A selected fluorescent agent preferably has the following properties: approval by government regulatory authorities (e.g., FDA); bio-compatible in such a way that remaining traces of the fluorescent agent on an article can be safely introduced into the human body without incurring health problems; binds rapidly to proteins (e.g., within a few seconds); has the ability to withstand exposure to harsh washing environment conditions (i.e., harsh chemicals and temperatures exceeding 80° C.); water soluble; and high quantum yield. Alternative fluorophores include, but are not limited to, rose bengal, acid red, phtalocyanine, and luminol.

While the present invention has been described in connection with the use of a fluorescent agent, it is also contemplated that the present invention may be adapted for use with alternative chemical agents that provide luminescence, including but not limited to, chemical agents which provide phosphorescence, chemiluminescence, or bioluminescence.

Referring now to FIGS. 1 and 3, one or more articles 10 (e.g., a tool or instrument) which have been exposed to a solution containing fluorescein are placed in a tray 5. The articles are preferably arranged in a single layer to provide exposure to the light emitted by the light source, as will be described below.

An operator of soil detection system 30 grabs handle grip 84 to manually move scanning unit 80 over the surfaces of an article 10 while activating laser 100 using trigger switch 86. Activation of trigger switch 86 causes laser 100 to produce a laser light 102 at a wavelength of 488 nm (blue light). The laser light 102 is reflected by dichroic beamsplitter 116 and travels through opening 81a of housing 81 and is directed toward article 10.

Figure 6A:
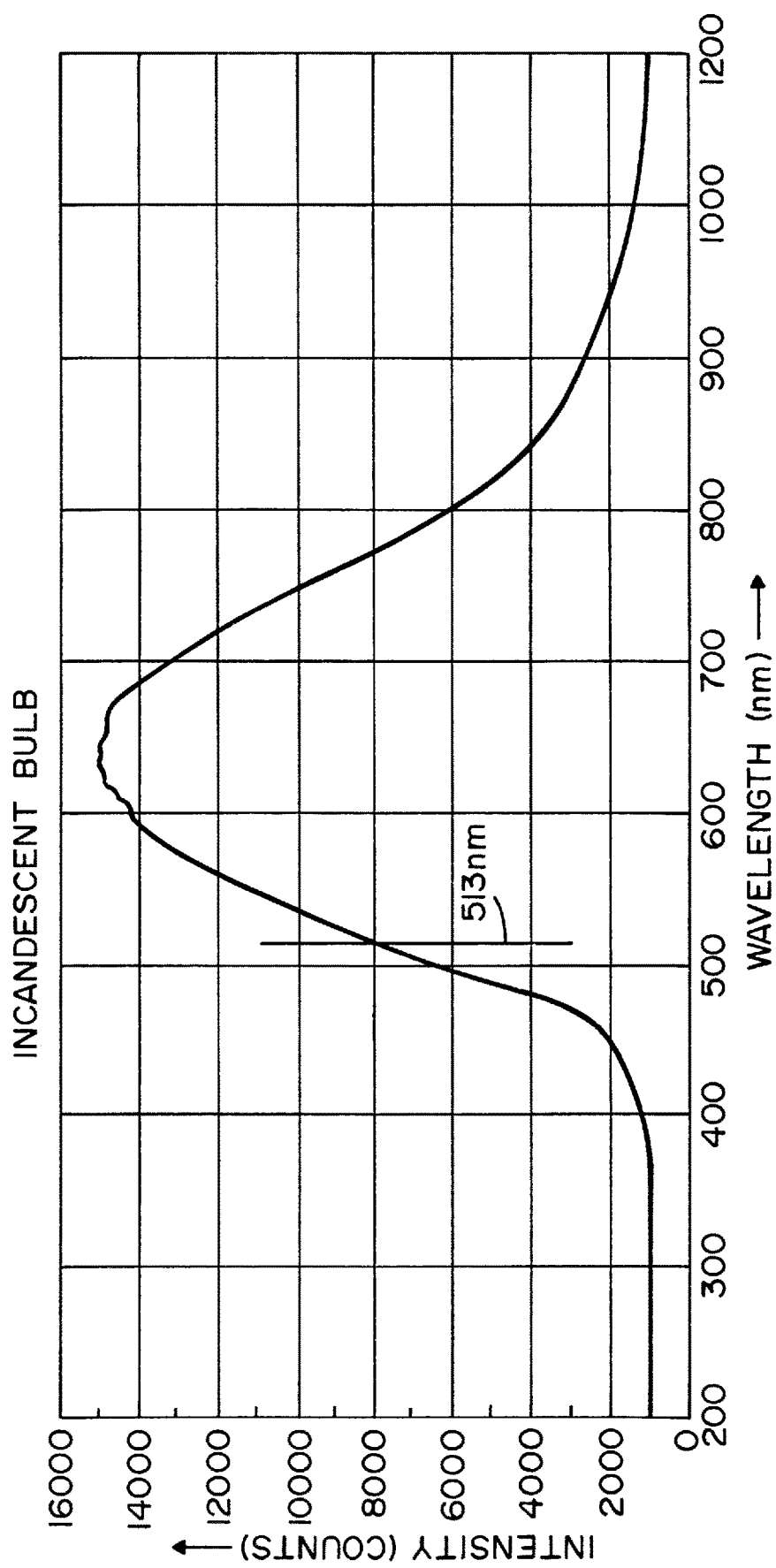
FIG. 6A is a graph illustrating the intensity of light emitted by an incandescent light bulb for a range of wavelengths.
Figure 6B:
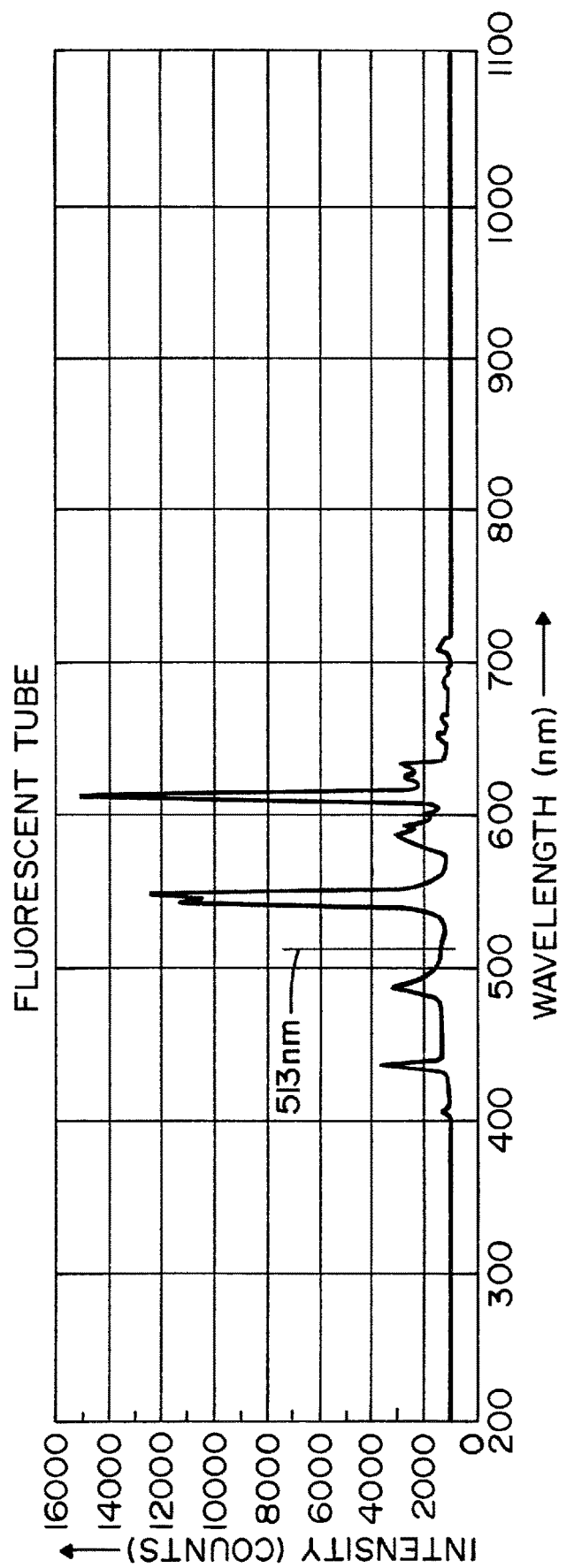
FIG. 6B is a graph illustrating the intensity of light emitted by a fluorescent light tube for a range of wavelengths.
Figure 6C:
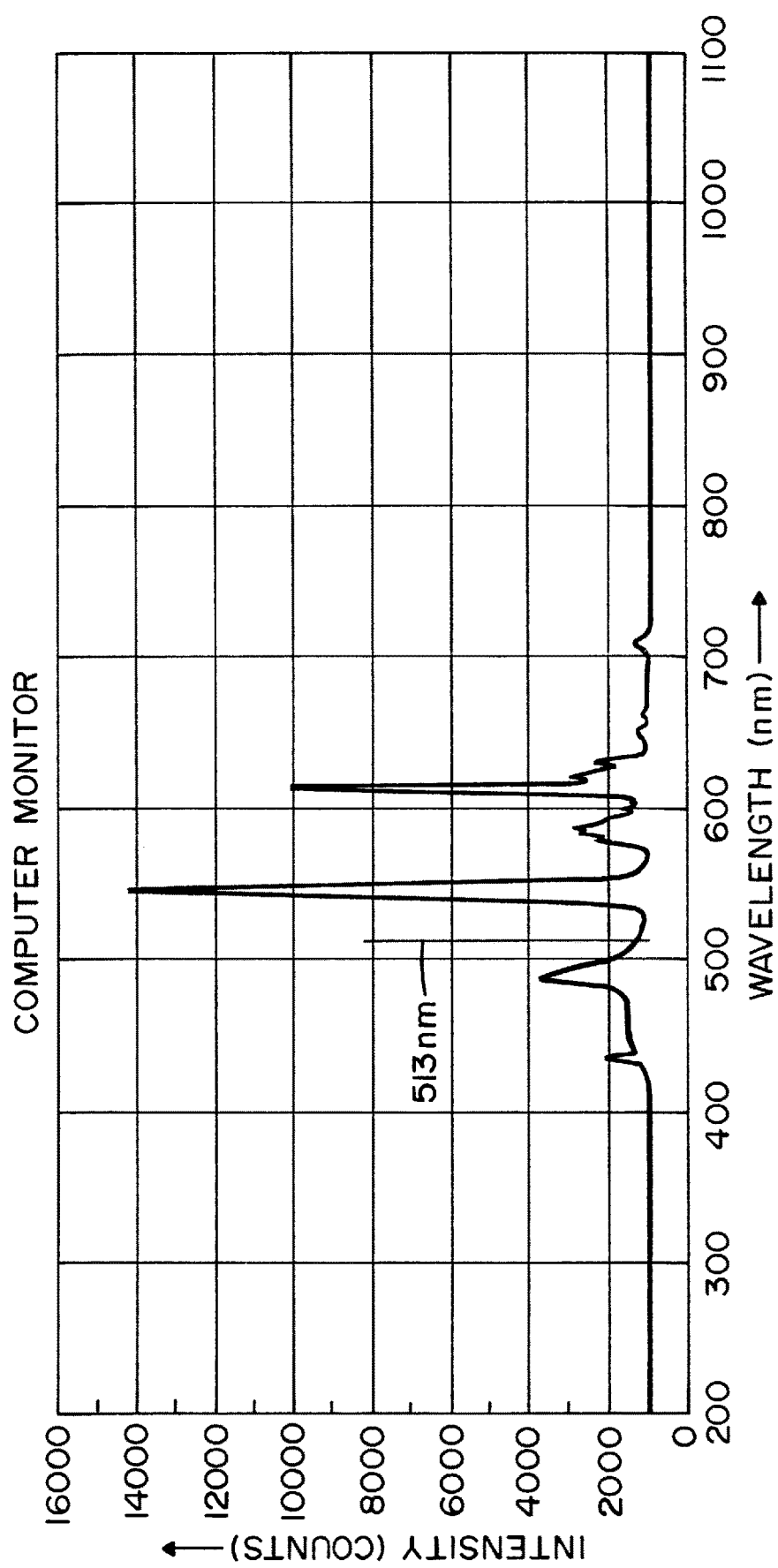
FIG. 6C is a graph illustrating the intensity of light emitted by a computer monitor for a range of wavelengths.

Article 10 is exposed to both ambient light and laser light 102 as scanning unit 80 is moved over the surfaces of article 10. FIGS. 6A-6C show the intensity of ambient light produced at various wavelengths for ambient lighting sources, such as an incandescent bulb, a fluorescent tube light, and a computer monitor screen, respectively. As discussed above, when the fluorescein that binds to soil is exposed to the laser light 102 at a wavelength of about 490 nm, the fluorescein emits light (i.e., fluoresces) at a wavelength of about 513 nm.

Reflected ambient light ($L_R$) and fluorescent light ($L_F$) emitted by the excited fluorescein pass through dichroic beamsplitter 116 and filter 112 before traveling through lens 94 of detector 90. Filter 112 allows only red and green light to pass therethrough to detector 90. The light transmitted through lens 94 is received by image sensor 92.

As scanning unit 80 is moved across article 10, the user squeezes trigger 86, thereby activating laser 100 to produce laser light 102 that is emitted from housing 81 through opening 81a. Laser light 102 is incident on article 10 as scanning unit is moved across article 10. Ambient light is also incident upon article 10, thereby producing ambient light reflections that will include both red and green light. When the fluorescent agent (i.e., fluorescein) present in the soil is excited by laser light 102 the soil fluoresces thereby emitting light at a wavelength of about 513 nm (green light). Both the reflected ambient light ($L_R$) and the fluorescent light ($L_F$) of the soil pass through filter 112 which filters out all but red and green light. Therefore, image sensor 92 only receives red and green light.

Referring now to FIG. 1, there is shown a sample input spectrum 120. As scanning unit 80 is moved across article 10, image sensor 92 acquires and transmits to control unit 40 detected light data indicative of input spectrum 120 that includes a green light waveform 122 and a red light waveform 124. Green light waveform 122 is indicative of the intensity of green light detected by image sensor 92 and red light waveform 124 is indicative of the intensity of red light detected by image sensor 92.

Control unit 40 is programmed to spectrally discriminate between soil fluorescence (indicating the presence of soil) and specular ambient light reflections, based upon the measure of saturation of green light intensities relative to red light intensities (ratio). In the illustrated embodiment, the range of this measure of saturation is enclosed between zero and one. Accordingly, the system is robust to the variations of ambient light of the surrounding environment and changes of acquisition parameters. A value of saturation close to zero is indicative of the presence of specular ambient light reflections, whereas a large value close to one is indicative of the presence of soil.

Control unit 40 may be programmed to display the detected light data to a user on display unit 42. Control unit 40 may also be programmed to provide the user with a visual and/or audible indicator (e.g., warning/alarm/feedback) via display unit 42 and audio output 48 in the event that the ratio of green light intensity-to-red light intensity indicates the presence of soil. It is further contemplated that control unit 40 may present an image of article 10 and use display unit 42 to display the location of the detected soil (i.e., contaminated region) on article 10. The image of article 10 may be acquired during optical scanning of article 10 or from a prestored image library comprised of images of a plurality of commonly used articles 10.

Figure 2:
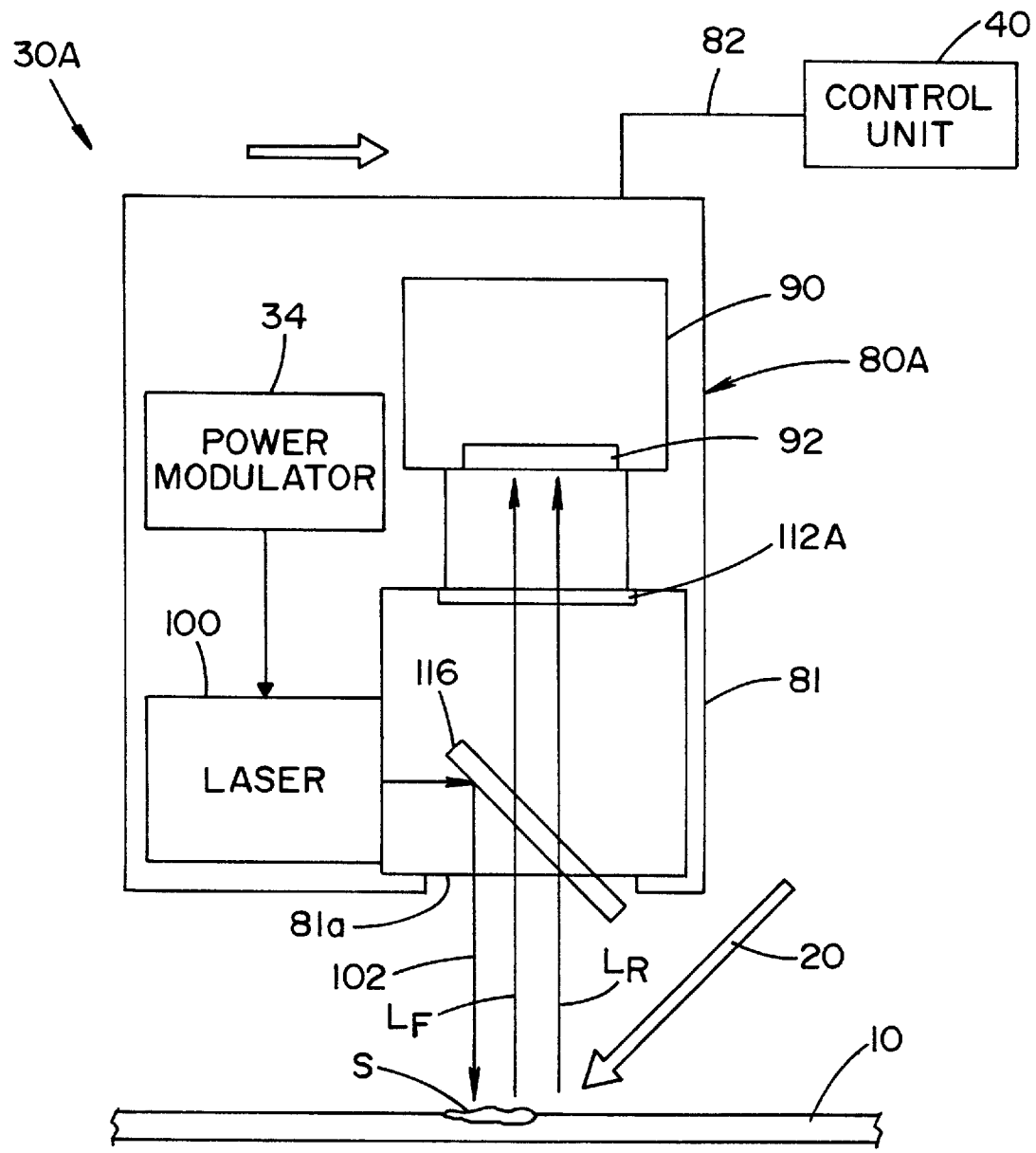
FIG. 2 is a schematic view of a soil detection system according to a second embodiment of the present invention.

Referring now to FIG. 2, there is shown a soil detection system 30A according to an alternative embodiment of the present invention. Soil detection system 30A is similar to soil detection system 30 in several regards, and thus like components have been given the same reference numbers. Soil detection system 30A includes scanning unit 80A having laser 100, detector 90, a power modulator 34, dichroic beamsplitter 116, and a light filter 112A that allows only green light to pass therethrough. Power modulator 34 produces a pulsed waveform that provides an ON/OFF signal to activate/deactivate laser 100. When the pulse is an ON signal, laser 100 is activated to produce laser light 102. The pulsed waveform causes laser 100 to be continuously pulsed ON and OFF at a laser modulation frequency. As scanning unit 80A is moved across article 10, the user squeezes trigger 86, thereby activating power modulator 34 to produce the pulsed waveform that provides the ON/OFF signal to laser 100. When the pulse is an ON signal, laser light 102 is emitted from housing 81 through opening 81a. It should be appreciated that power modulator 34 may alternatively take the form of a square wave modulation circuit to modulate the output of laser 100 (amplitude modulation).

Laser light 102 is incident on article 10 as scanning unit is moved across article 10. Ambient light is also incident upon article 10, thereby producing ambient light reflections that will include green light. When the fluorescent agent (e.g., fluorescein) present in the soil is excited by laser light 102 the soil fluoresces thereby emitting light at a wavelength of about 513 nm (green light). Both the reflected ambient light ($L_R$) and the fluorescent light ($L_F$) of the soil passes through filter 112 which filters out all but green light. Therefore, image sensor 92 only receives green light. In this embodiment, image sensor may take the form of a color or gray-scale type sensor.

The modulation frequency for laser 100 is set to be lower than the emission frequencies of ambient lighting sources. Detector 90 operates in a continuous (video) mode at a frame rate that is higher that the modulation frequency. Green blinking features on display unit 42 of control unit 40 at the modulation frequency are indicative of soil. Non-blinking features or blinking at frequencies other than the modulation frequency are identified as ambient light reflections. In one embodiment of the present invention the modulation frequency is around 10 Hz. The frequency of ambient lighting sources are $f$=20-60 kHz (electronic ballast fluorescent tube), $f$=120 Hz (incandescent light bulb and magnetic ballast fluorescent tube), and $f$=240 Hz (computer monitor).

As scanning unit 80A is moved across article 10, power modulator 34 produces the pulsed waveform that causes detector 90 and laser 100 to be continuously pulsed ON and OFF. As indicated above, filter 112A only allows green light to pass therethrough to detector 90. Image sensor 92 acquires and transmits to control unit 40 detected light data indicative of the intensity of green light detected by image sensor 92.

Figure 5:
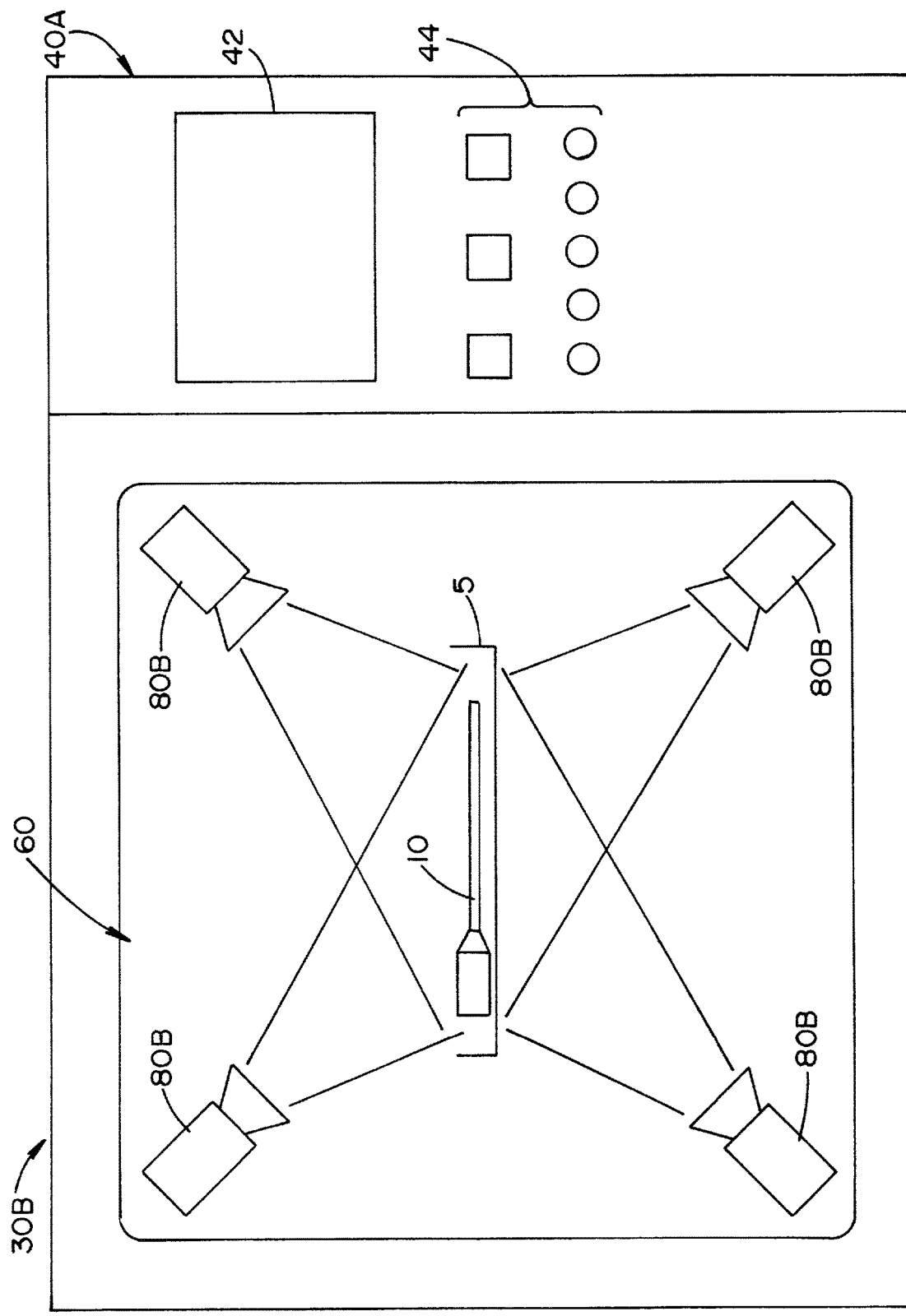
FIG. 5 illustrates a soil detection system according to an alternative embodiment of the present invention.

FIG. 5 illustrates a soil detection system 30B according to an alternative embodiment of the present invention. Soil detection system 30B includes a control unit 40A having an inspection chamber 60 for inspecting articles 10 placed on a tray 5. A plurality of scanning units 80B are located within chamber 60 for exposing the plurality of surfaces of an article 10 to laser light 102. Scanning units 80B are similar in most respects to scanning units 80 and 80A except that they are automatically activated by control unit 40A. The embodiment shown in FIG. 5 eliminates the need for the user to manually activate a handheld scanning unit 80, 80A and manually expose all of the surfaces of an article 10 to laser light 102.

It is contemplated that tray 5 may also be connected with an apparatus (now shown) for rotating, shaking, or otherwise moving tray 5 within chamber 60. It is further contemplated that scanning units 80B may be mounted to moveable arms (not shown) to provide a range of motion for each scanning unit 80B. Control unit 40 is programmed to control movement of tray 5 and scanning units 80B.

The foregoing description discloses specific embodiments of the present invention. It should be appreciated that these embodiment are described for purposes of illustration only, and that numerous alterations and modifications may be practiced by those skilled in the art without departing from the spirit and scope of the invention. For example, it is contemplated that the scanning unit of the present invention could communicate with the control unit via wireless communications. It is also contemplated that the method and apparatus of the present invention may also be used in combination with automated and human visual inspections using "white light" imaging. In addition, it is further contemplated that the present invention may be adapted to include a fiber optic accessory for point inspection of canulated instruments. It is intended that all such modifications and alterations be included insofar as they come within the scope of the invention as claimed or the equivalents thereof.

Having described the invention, the following is claimed:

1. A soil detection system for detecting presence of soil on an article treated with a fluorescent agent bound to soil present on the article, the soil detection system comprising:
   a scanning unit for scanning the article, the fluorescent agent emitting fluorescent light at a fluorescence wavelength, the scanning unit including:
      a light source for producing laser light at an excitation wavelength for the fluorescence wavelength to be incident on the article,
      a light filter for filtering out light emanating from said article except for light emanating from said article at first and second predetermined wavelengths, said light emanating from said article at said first and second predetermined wavelengths being allowed to pass through said light filter, said second predetermined wavelength corresponding to the fluorescence wavelength, said light emanating from said article including ambient light reflected by the article and light emitted by exciting the fluorescent agent bound to the soil with the laser light;
      a light detector for detecting the filtered light allowed to pass through said light filter and generating light data corresponding thereto, and a control unit configured to receive the generated light data and, using the received light data, spectrally discriminate between soil fluorescence and ambient light reflections based upon a value of saturation of intensities of the filtered light at the first predetermined wavelength contained in the generated light data relative to intensities of the filtered light at the second predetermined wavelength contained in the generated light data to determine the presence of soil on the article.

2. A soil detection system according to claim 1, wherein the first and second predetermined wavelengths respectively comprise a red light wavelength and a green light wavelength.

3. A soil detection system according to claim 2, wherein said light detector is an image sensor that transmits the generated light data to the control unit, the generated light data being indicative of an input spectrum that includes a green light waveform and a red light waveform,
  wherein the green light waveform is indicative of the intensities of the filtered light at the second predetermined wavelength contained in the generated light data, and
  wherein the red light waveform is indicative of the intensities of the filtered light at the first predetermined wavelength contained in the generated light data.

4. A soil detection system according to claim 2, wherein said intensities of the filtered light at the second predetermined wavelength are green light intensities relative, and
  wherein said intensities of the filtered light at the first predetermined wavelength are red light intensities.

5. A soil detection system according to claim 4, wherein said control unit measures the value of saturation as a ratio such that a value of saturation close to zero is indicative of the presence of specular ambient light reflections, whereas a large value close to one is indicative of the presence of soil.

6. A soil detection system according to claim 1, wherein said scanning unit is a handheld scanning unit moved across the article by a user, so that the light detector acquires and transmits to the control unit the generated light data indicative of the filtered light.

7. A soil detection system according to claim 1, wherein said control unit includes an inspection chamber having at least one scanning unit therein.

8. A soil detection system according to claim 1, wherein said control unit includes an audio output to provide an audible feedback if soil is detected.

9. A soil detection system according to claim 1, wherein said control unit includes a display unit to provide a visual feedback if soil is detected.

10. A soil detection system according to claim 1, wherein said article is a stainless steel surgical instrument.

11. A soil detection system according to claim 1, wherein said laser is a laser diode that predominantly emits light at wavelengths of 488.

12. A soil detection system according to claim 1, wherein said fluorescent agent binds to proteins.

13. A soil detection system according to claim 1, wherein said detector includes a CMOS image sensor or a CCD image sensor.

* * * * *